US012730113B2

(12) United States Patent
Teramoto

(10) Patent No.: US 12,730,113 B2
(45) Date of Patent: Sep. 8, 2026

(54) RIBOSOMAL PROTEIN JUDGEMENT METHOD, BIOLOGICAL SPECIES IDENTIFICATION METHOD, AND MASS SPECTROMETRY APPARATUS

(71) Applicant: SHIMADZU CORPORATION, Kyoto (JP)

(72) Inventor: Kanae Teramoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 943 days.

(21) Appl. No.: 18/078,171

(22) Filed: Dec. 9, 2022

(65) Prior Publication Data

US 2024/0192222 A1 Jun. 13, 2024

(51) Int. Cl.
*G01N 33/68* (2006.01)
*H01J 49/00* (2006.01)
*H01J 49/16* (2006.01)

(52) U.S. Cl.
CPC ...... *G01N 33/6851* (2013.01); *H01J 49/0036* (2013.01); *H01J 49/164* (2013.01)

(58) Field of Classification Search
None
See application file for complete search history.

(56) References Cited

PUBLICATIONS

Dekio, I. et al. What Do We See in Spectra?: Assignment of High-Intensity Peaks of Cutibacterium and *Staphylococcus* Spectra of MALDI-TOF Mass Spectrometry by Interspecies Comparative Proteogenomics, Microorganisms 2021, 9, 1243 (Year: 2021).*

Kanae Teramoto et al., "Comparative Characterization of Ribosomal Proteins of Lactic Acid Bacteria by Matrix-Assisted Laser Desorption/Ionization Mass Spectrometry", J. Mass Spectrom. Soc. Jpn., 2008, 11 pages, vol. 56, No. 1.

Kanae Teramoto et al., "Progress in Rapid Identification and Classification of Bacteria by Mass Spectrometry", J. Mass Spectrom. Soc. Jpn., 2008, pp. 83-90, vol. 56, No. 3.

Victor Ryzhov et al., "Characterization of the Protein Subset Desorbed by MALDI from Whole Bacterial Cells", Analytical Chemistry, 2001, pp. 746-750, vol. 73, No. 4.

Office Action issued Jun. 27, 2023 in Japanese Application No. 2020-096967.

* cited by examiner

*Primary Examiner* — Xiaoyun R Xu
(74) *Attorney, Agent, or Firm* — Sughrue Mion, PLLC

(57) ABSTRACT

Provided is a ribosomal protein judgement method, comprising: an attribution step that involves comparing observed m/z values indicated by peaks on a mass spectrum detected by mass spectrometry of a sample containing ribosomal proteins, with first calculated m/z values based on a database, and attributing at least some of the peaks thus detected to ribosomal proteins; and a presumption step that involves presuming a protein corresponding to a peak with a relative intensity from 50 to 150% relative to an approximate curve or an approximate straight line plotted with relative intensities of the peaks attributed to ribosomal proteins, to be a ribosomal protein.

13 Claims, 6 Drawing Sheets

PROCESSING MEMBER

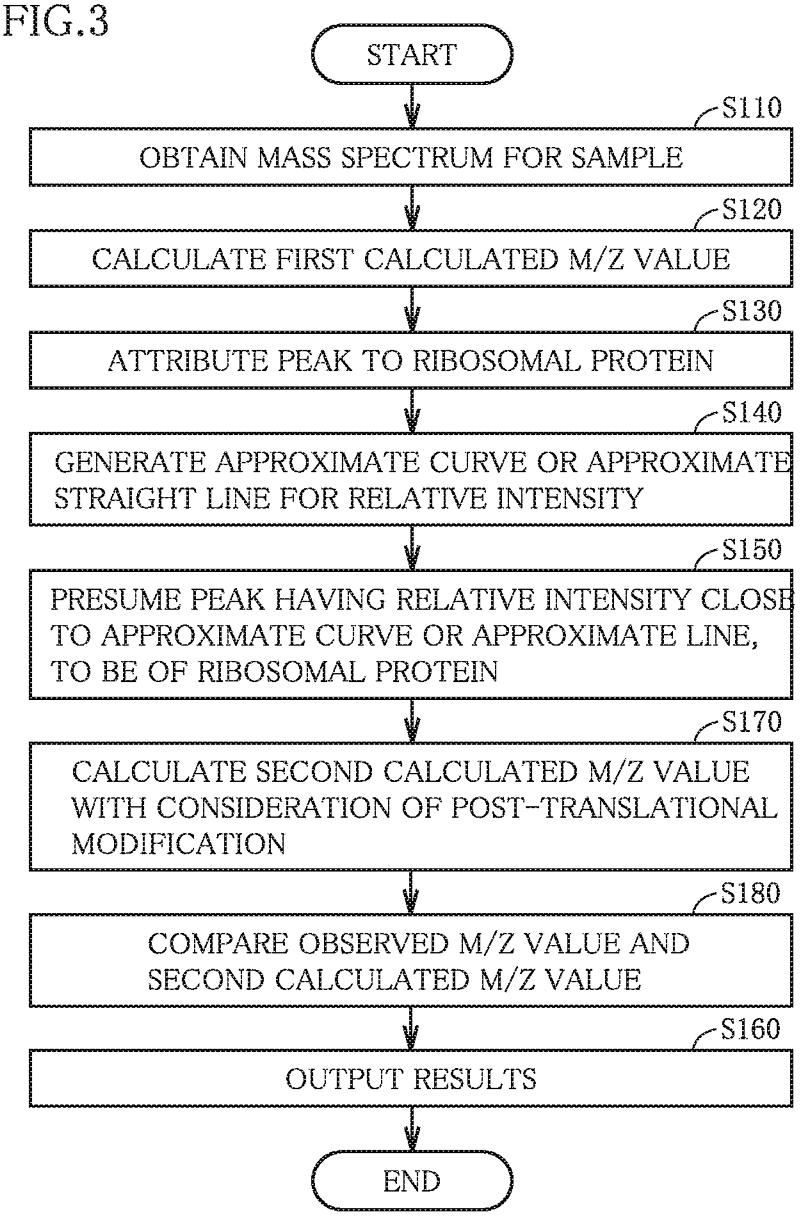
FIG.3
START
S110
OBTAIN MASS SPECTRUM FOR SAMPLE
S120
CALCULATE FIRST CALCULATED M/Z VALUE
S130
ATTRIBUTE PEAK TO RIBOSOMAL PROTEIN
S140
GENERATE APPROXIMATE CURVE OR APPROXIMATE STRAIGHT LINE FOR RELATIVE INTENSITY
S150
PRESUME PEAK HAVING RELATIVE INTENSITY CLOSE TO APPROXIMATE CURVE OR APPROXIMATE LINE, TO BE OF RIBOSOMAL PROTEIN
S170
CALCULATE SECOND CALCULATED M/Z VALUE WITH CONSIDERATION OF POST-TRANSLATIONAL MODIFICATION
S180
COMPARE OBSERVED M/Z VALUE AND SECOND CALCULATED M/Z VALUE
S160
OUTPUT RESULTS
END

RIBOSOMAL PROTEIN JUDGEMENT METHOD, BIOLOGICAL SPECIES IDENTIFICATION METHOD, AND MASS SPECTROMETRY APPARATUS

BACKGROUND OF THE INVENTION

Field of the Invention

The present invention relates to a ribosomal protein judgement method, a biological species identification method, and a mass spectrometry apparatus.

Description of the Background Art

For identifying bacterial species by mass spectrometry, a method is known that involves using a ribosomal protein as a biomarker. For example, Kanae Teramoto, et. al., "Comparative Characterization of Ribosomal Proteins of Lactic Acid Bacteria by Matrix-Assisted Laser Desorption/Ionization Mass Spectrometry", J Mass Spectrom. Soc. Jpn, Vol. 56, No. 1, 2008 (NPL 1) and Kanae Teramoto and Hiroaki Sato, "Progress in Rapid Identification and Classification of Bacteria by Mass Spectrometry", J Mass Spectrom. Soc. Jpn, Vol. 56, No. 3, 2008 (NPL 2) disclose a method that involves comparing observed masses of ribosomal proteins of a bacterium observed on a mass spectrum, with calculated masses determined from amino acid sequences registered in protein databases, to select a biomarker that is suitable for rapid identification of the bacterium, and a method for identifying a bacterial species that gives the amino acid sequence information.

However, it is often the case that calculated masses of proteins calculated from databases do not match their actual, observed masses. This mismatch seems to be caused by, for example, the fact that amino acid sequences registered in databases are produced by mechanical translation of DNA sequences of genes without consideration of post-translational modification of the proteins. The number of proteins that have matching calculated mass and observed mass and thereby can be judged as ribosomal proteins has been limited, and for this reason, the accuracy of bacterial species identification has been limited.

With this regard, it was assumed that masses of proteins can be calculated with consideration of post-translational modification to successfully perform ribosomal protein judgement. However, there may be complex combinations of different types and patterns of post-translational modification, and therefore, it is not regarded as proper to calculate masses of many ribosomal proteins with consideration of possible post-translational modification and compare the resultant masses with observed masses to judge whether they are ribosomal proteins or not.

An object of the present invention is to provide a method for easily judging whether a protein indicated by a peak on a mass spectrum generated by mass spectrometry is a ribosomal protein or not.

SUMMARY OF THE INVENTION

The present invention relates to a ribosomal protein judgement method comprising: an attribution step that involves comparing observed m/z values indicated by peaks on a mass spectrum detected by mass spectrometry of a sample containing ribosomal proteins, with first calculated m/z values based on a database, and attributing at least some of the peaks thus detected to ribosomal proteins; and a presumption step that involves presuming a protein corresponding to a peak with a relative intensity from 50 to 150% relative to an approximate curve or an approximate straight line plotted with relative intensities of the peaks attributed to ribosomal proteins, to be a ribosomal protein.

The present invention also relates to a mass spectrometry apparatus comprising: a mass separation member that separates ions based on m/z values; a detection member that detects the ions separated by the mass separation member, a mass spectrum generation member that generates a mass spectrum based on the ions detected by the detection member; and a judgement member that determines, from the mass spectrum, peaks that are attributable to ribosomal proteins based on a database, generates an approximate curve or an approximate straight line for relative intensities of the peaks, and selects a peak with a relative intensity from 50 to 150% relative to the approximate curve or the approximate straight line.

The present invention also relates to a program that causes a processing apparatus to perform processing that involves determining, from the mass spectrum obtained by the mass spectrometry apparatus, peaks attributable to ribosomal proteins based on a database, generating an approximate curve or an approximate straight line for relative intensities of the peaks, and selecting a peak with a relative intensity from 50 to 150% relative to the approximate curve or the approximate straight line.

The present invention allows for easily judging whether a protein indicated by a peak on a mass spectrum obtained by mass spectrometry is a ribosomal protein or not.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a flowchart showing the flow of a ribosomal protein judgement method according to an embodiment.

DESCRIPTION OF THE PREFERRED EMBODIMENTS

Figure 1:
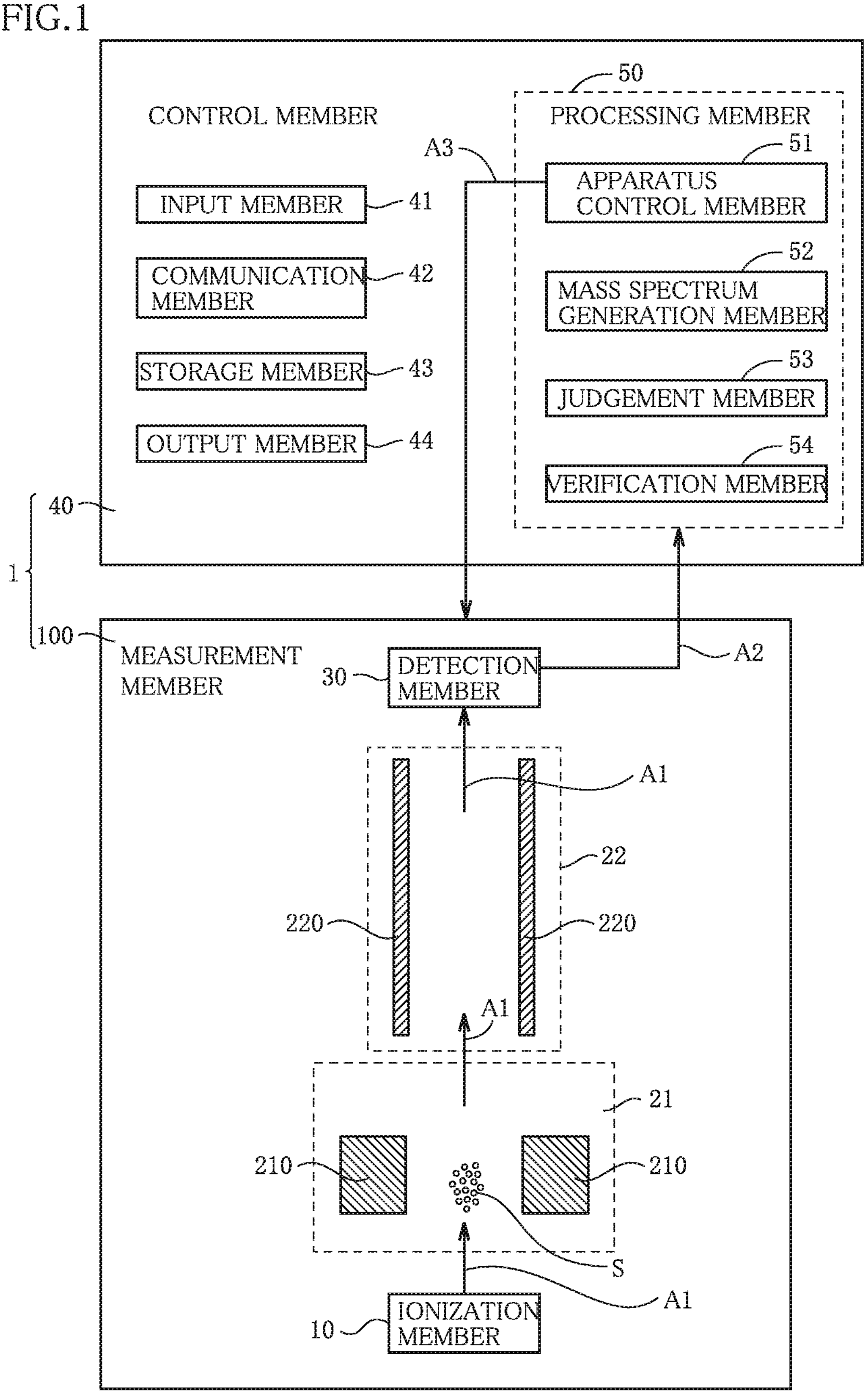
FIG. 1 shows the schematic configuration of a mass spectrometry apparatus for a ribosomal protein judgement method according to an embodiment.

A ribosomal protein judgement method according to the present invention comprises:

- an attribution step that involves comparing observed m/z values indicated by peaks on a mass spectrum detected by mass spectrometry of a sample containing ribosomal proteins, with first calculated m/z values based on a database, and attributing at least some of the peaks thus detected to ribosomal proteins; and
- a presumption step that involves presuming a protein corresponding to a peak with a relative intensity from 50 to 150% relative to an approximate curve or an approximate straight line plotted with relative intensities of the peaks attributed to ribosomal proteins, to be a ribosomal protein.

The ribosomal protein judgement method according to the present invention allows for easily judging whether a protein indicated by a peak on a mass spectrum obtained by mass spectrometry is a ribosomal protein or not. Ribosomes are constituted of at least 50 types of proteins, and the proteins are present in approximately equimolar amounts. Because of this, it is ideally expected that, when a sample containing ribosomal proteins is subjected to mass spectrometry, the peaks of the ribosomal proteins on the mass spectrum have approximately the same relative intensity. From this, it can be judged that a peak having approximately the same relative intensity as the relative intensity of a peak attributed to a ribosomal protein is highly likely to be of a ribosomal protein.

In the following, each step will be described in detail.

[Attribution Step]

The attribution step compares observed m/z values indicated by peaks on a mass spectrum detected by mass spectrometry of a sample containing ribosomal proteins, with first calculated m/z values based on a database, and attributes at least some of the peaks thus detected to ribosomal proteins.

The first calculated m/z values can be calculated from amino acid sequence information retrieved from a database such as GenBank, RefSeq, TPA, SwissProt, PIR, PRF, and PDB. In such a database, at least one selected from amino acid sequences of proteins and DNA sequences of genes is registered. The database includes information regarding taxa (such as family, genus, and species) of cells. The first calculated m/z values may be calculated with consideration of post-translational modification. It is because this allows for more matches to be found between observed m/z values and first calculated m/z values to increase the number of peaks, among other peaks detected on a mass spectrum, that are attributable to ribosomal proteins. The post-translational modification is preferably N-terminal methionine cleavage. This is because ribosomal proteins often have N-terminal methionine cleavage as post-translational modification. Especially for bacteria, many of the first calculated m/z values calculated with consideration of N-terminal methionine cleavage match observed m/z values, resulting in successful attribution of most ribosomal protein peaks. It is known that N-terminal methionine tends to be cleaved when the second amino acid residue is glycine (G), alanine (A), serine (S), proline (P), valine (V), threonine (T), or cysteine (C). However, N-terminal methionine cleavage may not always occur even when one of these amino acid residues is at the second position.

Herein, when the difference between a calculated m/z value and an observed m/z value is 500 ppm or less according to an external standard method, it is determined that the calculated m/z value matches the observed m/z value. Preferably, the calculated m/z value of a protein thus matched is used for performing self calibration of the attributed peak to check that the difference between the calculated m/z value and the observed m/z value of the peak used for the self calibration is 200 ppm or less.

From the viewpoint of containing equimolar amounts of ribosome-constituting ribosomal proteins, the sample preferably contains ribosomal proteins of cell origin. The sample may contain the entire ribosomes or the entire cells.

The sample may be of prokaryote origin, or may be of eukaryote origin. The sample is preferably microorganism origin, which may include an unknown microorganism. The prokaryote includes bacteria and archaea. The bacteria include bacteria of the genus *Escherichia* (such as *Escherichia coli*), bacteria of the genus *Bacillus* (such as *Bacillus subtilis*), bacteria of the genus *Lactobacillus* (such as lactic acid bacteria), bacteria of the genus *Synechocystis* (such as cyanobacteria), bacteria of the genus *Mycobacterium* (such as actinomycete), and the like. The archaea include *Methanopyrus, Methanococcus, Thermococcus, Pyrococcus*, and the like. The eukaryote includes animals, plants, fungi, and protists. The fungi include filamentous fungi, yeasts, mushrooms, molds, and the like, including Chytridiomycota, Zygomycota, Ascomycota, Basidiomycota, Glomeromycota, Microsporidia, and the like. Ascomycota includes *Aspergillus* (such as *Aspergillus oryzae*), *Penicillium* (such as *Penicillium notatum*), *Saccharomyces* (such as budding yeast), and the like. As compared to bacteria, eukaryotes are considered to have less peaks that can be attributed to ribosomal proteins with consideration of N-terminal methionine cleavage alone. It is because ribosomal proteins of eukaryotes, including fungi, often have complex post-translational modification as compared to ribosomal proteins of prokaryotes and, therefore, the first calculated m/z values calculated from a database tend to differ from the observed m/z values obtained by mass spectrometry. The ribosomal protein judgement method according to the present invention allows for easily judging whether a protein indicated by a peak on a mass spectrum is a ribosomal protein or not even when a sample of eukaryote origin is used.

The sample may be prepared as appropriate from cells, and, for example, the sample may be a protein fraction extracted from cells, preferably a ribosomal protein fraction. When a ribosomal protein fraction is used as a sample, the proportion of ribosomal proteins contained in the sample is relatively high, enabling more accurate judgement on ribosomal proteins. The method for fractioning ribosomal proteins is not particularly limited as long as it can extract or concentrate ribosomal proteins, and examples thereof include a method involving cell disruption and ultrafiltration processing, a method involving ultracentrifugation, and the like.

The mass spectrometry is not particularly limited as long as it is a mass spectrometry method capable of quantitatively measuring ribosomal proteins, and a preferable method is a mass spectrometry method involving soft ionization which tends not to cause degradation of high-molecular-weight compounds. Examples of such a mass spectrometry method include analytic methods such as matrix-assisted laser desorption/ionization mass spectrometry (MALDI-MS) and electrospray ionization mass spectrometry (ESI-MS). The mass spectrometry is preferably MALDI-MS. Most ribosomal proteins are basic proteins with high proton affinity and, therefore, tend to produce $[M+H]^+$ ions during MALDI. In addition, the molecular weights of ribosomal proteins fall within the range of approximately 5000 to 20000, and MALDI-MS can determine the masses of ribosomal proteins with a mere error of several Da. Therefore, when the mass spectrometry is MALDI-MS, ribosomal protein peak detection from a sample can be performed more easily and the difference between observed m/z values and first calculated m/z values can be decreased.

[Presumption Step]

The presumption step presumes a protein corresponding to a peak with a relative intensity from 50 to 150% relative to an approximate curve or an approximate straight line plotted with relative intensities of the peaks attributed to ribosomal proteins, to be a ribosomal protein.

Ribosomal proteins that constitute ribosomes exist in approximately equimolar amounts, as described above, so, ideally, peaks attributed to ribosomal proteins have approximately the same relative intensity. For example, when further preparing ribosome subunit proteins from ribosome fractions, separating the subunit proteins by liquid chromatography (LC), subjecting the samples to mass spectrometry together with a reference material with known concentration to generate a mass spectrum, selecting peaks attributed to ribosomal proteins, and plotting the relative intensities on a scatter diagram to generate an approximate straight line, then, on the assumption that the ionization efficiency is constant, the resultant approximate straight line is a horizontal straight line (namely, the relative intensity is constant). However, even when detecting proteins that exist in equimolar amounts, the relative intensities of the peaks on the mass spectrum may not always be the same, depending of the detection method. For example, in the case of MALDI-MS, due to the effect of mass discrimination, a smaller m/z value is detected with a greater relative intensity and a greater m/z value is detected with a smaller relative intensity. Therefore, when a sample is measured by MALDI-MS, ribosomal proteins which exist in equimolar amounts are approximated to a straight line or a curve on which the greater the m/z value the smaller the relative intensity. Herein, when the correlation coefficient ($R^2$) is 0.70 or more, preferably 0.80 or more, it is determined that the approximate curve or the approximate straight line is sufficiently accurate.

From the unidentified peaks which are not attributed to ribosomal proteins based on their first calculated m/z values, peaks having relative intensities close to the approximate curve or the approximate straight line are presumed to be of ribosomal proteins. The expression "peaks having relative intensities close to the approximate curve or the approximate straight line" means that the relative intensities of the peaks are from 50 to 150%, preferably from 60 to 140%, more preferably from 70 to 130%, further preferably from 80 to 120%, most preferably from 90 to 110% of the relative intensities indicated by the approximate curve or the approximate straight line.

[Verification Step]

Preferably, the ribosomal protein judgement method further comprises a verification step that involves calculating a second calculated m/z value of the protein presumed to be a ribosomal protein, with consideration of post-translational modification, and comparing the second calculated m/z value with the observed m/z values. When the second calculated m/z value of a protein presumed to be a ribosomal protein calculated with consideration of post-translational modification matches an observed m/z value, the peak can be accurately judged to be of a ribosomal protein. In addition, information about ribosomal protein amino acid sequence and post-translational modification may also be obtained.

The second calculated m/z value is calculated with consideration of post-translational modification. Examples of the post-translational modification that should be considered here include N-terminal methionine cleavage, acetylation, methylation, phosphorylation, glycosylation, oxidation, ubiquitination, SUMOylation, lipidation, and a combination of these, and the like. The modification pattern of the post-translational modification that is taken into consideration in the verification step is different from the one in the attribution step. For example, when the calculation of the first calculated m/z value in the attribution step is performed with consideration of N-terminal methionine cleavage as post-translational modification, the calculation of the second calculated m/z value in the verification step is performed for a second calculated m/z value without N-terminal methionine cleavage or a second calculated m/z value with N-terminal methionine cleavage in combination with an additional post-translational modification. Because the presumption step has already selected peaks on a mass spectrum that are presumed to be of ribosomal proteins, it is not necessary to consider complex post-translational modification for all the peaks on the mass spectrum, and thereby, ribosomal protein judgement can be performed in an easier and more simple manner.

[Biological Species Identification Method]

A biological species identification method according to the present invention judges ribosomal proteins by using the above-described ribosomal protein judgement method, and identifies a species of a living thing that gives amino acid sequence information of the ribosomal proteins.

Ribosomal proteins are housekeeping genes which are involved in maintaining life and preserved very well across species. Ribosomal proteins are used as biomarkers for identification of biological species, because they can serve as a decisive index for assessing the difference between living things at the species level, based on minimal differences between amino acid sequences and the resulting differences between masses. In addition, ribosomes are structures abundant within cells and, therefore, ribosomal proteins can be easily detected by mass spectrometry.

The ribosomal protein judgement method described above allows for increasing the number of proteins that are judged as ribosomal proteins, making it possible to perform biological species identification in a way that is easier, more simple, and more accurate. The living thing as the identification target is preferably a microorganism that is too small to distinguish by the naked eye. The biological species identification method according to the present invention also allows for screening for useful microorganisms.

Especially when MALDI-MS is used as mass spectrometry, minimal mutations in the amino acid sequences of ribosomal proteins can be easily detected as peak shifts. The biological species identification method according to the present invention allows for distinguishing not only between species but also between subspecies and between highly-related strains.

[Mass Spectrometry Apparatus]

As an example of the ribosomal protein judgement method, a ribosomal protein judgement method using a mass spectrometry apparatus will be described below.

A mass spectrometry apparatus according to an aspect of the present invention comprises:

a mass separation member that separates ions based on m/z values;

a detection member that detects the ions separated by the mass separation member;

a mass spectrum generation member that generates a mass spectrum based on the ions detected by the detection member; and a judgement member that determines, from the mass spectrum, peaks that are attributable to ribosomal proteins based on a database, generates an approximate curve or an approximate straight line for relative intensities of the peaks, and selects a peak with a relative intensity from 50 to 150% relative to the approximate curve or the approximate straight line.

This mass spectrometry apparatus allows for easily judging whether a protein indicated by a peak on a mass spectrum obtained by mass spectrometry is a ribosomal protein or not.

FIG. 1 shows the schematic configuration of a mass spectrometry apparatus 1 according to an embodiment. Mass spectrometry apparatus 1 comprises a measurement member 100 and a control member 40. Part of or all of the function of control member 40 may be allocated to an electronic computer, a server, and/or the like that is physically separated from measurement member 100.

Measurement member 100 comprises an ionization member 10 that produces sample-originated protein ions S, an ion acceleration member 21, a mass separation member 22, and a detection member 30. The sample that is to be measured by measurement member 100 contains ribosomal proteins. The movement of protein ions S produced by ionization member 10 is schematically shown with arrows A1.

Control member 40 comprises an input member 41, a communications member 42, a storage member 43, an output member 44, and a processing member 50. Processing member 50 comprises an apparatus control member 51, a mass spectrum generation member 52, a judgement member 53, and preferably a verification member 54. The flow of the detection signal for protein ions S from detection member 30 of measurement member 100 is schematically shown with an arrow A2. Control of measurement member 100 by apparatus control member 51 is schematically shown with an arrow A3.

Ionization member 10 of measurement member 100 comprises a sample plate holder (not shown) for holding a sample plate, and an ion source that is equipped with a laser apparatus (not shown) for applying laser light to the sample plate, to ionize components of the sample by matrix-assisted laser desorption ionization (MALDI). As the method for sample ionization, any soft ionization method such as electrospraying (ESI) can be used in addition to MALDI. When ionization is performed by ESI, a configuration where mass spectrometry apparatus 1 further comprises a liquid chromatograph and components of the sample are separated by the liquid chromatograph and ionized by ionization member 10 is preferably adopted, from the perspective of achieving high separation capability.

After a sample is placed on the sample plate, a matrix is added to the sample, followed by drying. Subsequently, the sample plate is set on the sample plate holder inside a vacuum chamber of ionization member 10. The type of the matrix is not particularly limited, but from the viewpoint of efficient ionization of the protein sample, it is preferable to use sinapic acid, α-cyano-4-hydroxycinnamic acid (CHCA), or the like.

Ionization member 10 vacuums inside the vacuum chamber which contains the sample plate, and applies laser light to each sample on the sample plate to perform ionization in a sequential manner. The type of the laser apparatus for applying laser light is not particularly limited as long as it can oscillate the light that is to be absorbed by the selected matrix, and, for example, when the matrix contains sinapic acid or CHCA, $N_2$ laser (wavelength, 337 nm) and/or the like can be preferably used. Protein ions S thus ionized by ionization member 10 are extracted by an electric field produced by an extracting electrode and/or the like (not shown), and then introduced into ion acceleration member 21.

Ion acceleration member 21 comprises an accelerating electrode 210, and accelerates the introduced protein ions S. The flows of the accelerated protein ions S are converged as appropriate by an ion lens (not shown), and then introduced into mass separation member 22.

Mass separation member 22 comprises a flight tube 220, and separates the protein ions S according to the difference in the time of flight at the time when the protein ions S fly through flight tube 220. Although FIG. 1 shows a linear-type flight tube 220, a reflectron-type one, a multi-turn type one, and/or the like may also be used. The method for mass spectrometry is not particularly limited as long as it can separate and detect protein ions S contained in the sample.

Detection member 30 comprises an ion detector such as a multi-channel plate, and detects protein ions S separated by mass separation member 22 and outputs a detection signal whose intensity varies depending on the number of ions that enter into detection member 30. The detection signal thus output by detection member 30 is input into processing member 50 of control member 40.

Input member 41 of control member 40 comprises an input apparatus such as a mouse, a keyboard, various buttons, and/or a touch panel. Input member 41 receives, from a user, information necessary for controlling the operation of measurement member 100, information necessary for the processing that is run by processing member 50, and the like.

Communication member 42 of control member 40 comprises a communications apparatus capable of communicating via wireless and/or wired connection such as the Internet. Communication member 42 transmits and receives necessary data as appropriate; for instance, it receives data necessary for the processing that is run by judgement member 53 and verification member 54, and/or transmits data such as judgement results that has been processed by processing member 50.

Storage member 43 of control member 40 comprises a non-volatile storage medium. Storage member 43 stores calculated m/z values that are based on databases, mass spectra generated by mass spectrum generation member 52, measurement data output by measurement member 100, programs for the processing that is run by processing member 50, and the like.

Output member 44 of control member 40 comprises a display apparatus such as a liquid crystal monitor, a printer, and/or the like, to display on the display apparatus or to print on paper media the information regarding the measurement run by measurement member 100, the results produced by judgement member 53 and verification member 54, and the like.

Processing member 50 of control member 40 comprises a processor such as CPU, and is the mainstay of the operation of controlling mass spectrometry apparatus 1. Processing member 50 performs various processing by running programs stored by storage member 43 and/or the like.

Apparatus control member 51 of processing member 50 controls the operation of measurement member 100, based on data regarding measurement conditions that has been input via input member 41.

From the measurement data including the detection amounts of proteins detected by detection member 30 as well as the time of flight of these proteins, mass spectrum generation member 52 of processing member 50 converts the time of flight into m/z values, and generates a mass spectrum MS that shows detection amounts corresponding to the m/z values.

Judgement member 53 determines, from the mass spectrum, peaks that are attributable to ribosomal proteins based on a database, generates an approximate curve or an approximate straight line for relative intensities of the peaks, and selects a peak with a relative intensity from 50 to 150% relative to the approximate curve or the approximate straight line.

Judgement member 53 calculates first calculated m/z values of ribosomal proteins based on a database. In the database, at least one selected from amino acid sequences of proteins and DNA sequences of genes is registered, and based on this information, the first calculated m/z values are calculated. The first calculated m/z values may be calculated with consideration of post-translational modification. Preferably, the post-translational modification is N-terminal methionine cleavage. A list of observed m/z values of detected peaks on the mass spectrum is produced, which is then compared with the first calculated m/z values, and then the peaks of the matched observed m/z values are attributed to ribosomal proteins.

Judgement member 53 generates an approximate curve or an approximate straight line for relative intensities of the peaks attributed to ribosomal proteins. When the sample is measured by MALDI-MS, ribosomal proteins which exist in equimolar amounts are approximated to a straight line or a curve on which the greater the m/z value the smaller the relative intensity.

Judgement member 53 selects, from the unidentified peaks which are not attributed to ribosomal proteins based on their first calculated m/z values, peaks having relative intensities close to the approximate curve or the approximate straight line, to be of ribosomal proteins. The expression "peaks having relative intensities close to the approximate curve or the approximate straight line" means that the relative intensities of the peaks are from 50 to 150%, preferably from 60 to 140%, more preferably from 70 to 130%, further preferably from 80 to 120%, most preferably from 90 to 110% of the relative intensities indicated by the approximate curve or the approximate straight line.

Verification member 54 attributes the peak thus selected, to a ribosomal protein, with further consideration of post-translational modification.

Verification member 54 calculates a second calculated m/z value of a peak selected to be of a ribosomal protein by judgement member 53, preferably with consideration of post-translational modification. Examples of the post-translational modification that should be considered here include N-terminal methionine cleavage, acetylation, methylation, phosphorylation, glycosylation, oxidation, ubiquitination, SUMOylation, lipidation, and a combination of these, and the like.

Verification member 54 compares the second calculated m/z value calculated with consideration of post-translational modification, with the observed m/z values. When the second calculated m/z value calculated with consideration of post-translational modification matches an observed m/z value, the peak can be accurately judged to be of a ribosomal protein. In addition, information about ribosomal protein amino acid sequence and post-translational modification may also be obtained.

Processing member 50 may have a distinguishing member. The distinguishing member identifies, in a database, the species of the living thing that gives the amino acid information of the protein judged as a ribosomal protein. The greater the number of ribosomal proteins for which amino acid sequences are determined, the more enhanced the accuracy of the identification is. The processing that is run by the distinguishing member may be performed by a remote server.

Figure 2:
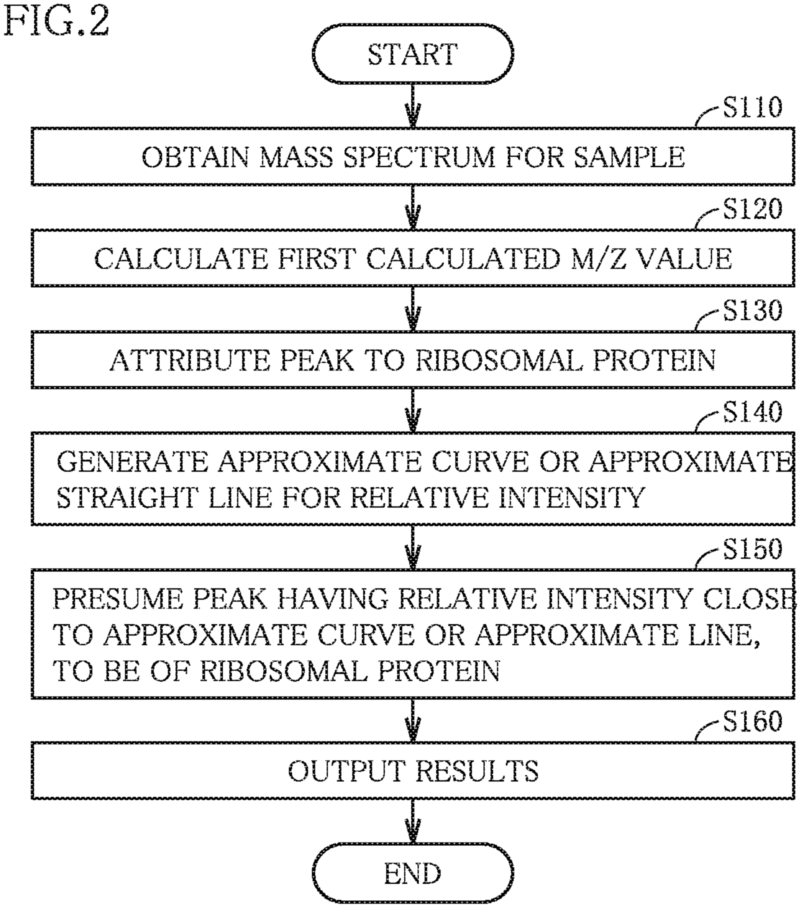
FIG. 2 is a flowchart showing the flow of a ribosomal protein judgement method according to an embodiment.

The flow of an example of the ribosomal protein judgement method is shown in the flowchart in FIG. 2.

Firstly, a sample is set in measurement member 100, and mass spectrometry is performed. In Step S110, mass spectrum generation member 52 generates a mass spectrum based on the signal retrieved by detection member 30.

In Step S120, first calculated m/z values are calculated based on a database. In Step S130, the first calculated m/z values thus calculated are compared with observed m/z values that are indicated by peaks on the mass spectrum, and matched peaks are attributed to ribosomal proteins.

In Step S140, an approximate curve or an approximate straight line for relative intensities of the peaks attributed to ribosomal proteins is generated. In Step S150, from the unidentified peaks which are not attributed to ribosomal proteins based on their first calculated m/z values, peaks having relative intensities close to the approximate curve or the approximate straight line are presumed to be of ribosomal proteins. The expression "peaks having relative intensities close to the approximate curve or the approximate straight line" means that the relative intensities of the peaks are from 50 to 150%, preferably from 60 to 140%, more preferably from 70 to 130%, further preferably from 80 to 120%, most preferably from 90 to 110% of the relative intensities indicated by the approximate curve or the approximate straight line. In Step S160, results are displayed on output member 44.

The flow of another example of the ribosomal protein judgement method is shown in the flowchart in FIG. 3. In FIG. 3, Step S170 and Step S180 are additionally carried out after the above-described Step S150. In Step S170, a second calculated m/z value of the protein presumed to be a ribosomal protein is calculated with consideration of post-translational modification. In Step S180, the second calculated m/z value thus calculated with consideration of post-translational modification is compared with the observed m/z values. A matched peak is judged to be of a ribosomal protein. In Step S160, results are displayed on output member 44.

[Program]

A program for achieving the information processing function of mass spectrometry apparatus 1 may be stored in a computer-readable storage medium, to cause a computer system to load and run a program stored in the storage medium that is for controlling the processing of, and related to, the above-described ribosomal protein judgement method and the above-described biological species identification method. Herein, the "computer system" includes hardware of OS (Operating System) and peripherals. The "computer-readable storage medium" refers to a transportable storage medium such as a flexible disk, a magneto-optical disk, an optical disk, and a memory card, and a storage apparatus such as a hard disk integrated in the computer system. The "computer-readable storage medium" may further include a communications line used for transmitting a program through a network such as the Internet and/or through a telecommunications line such as a telephone line, namely those for storing a program for a short period of time in a dynamic manner, as well as a volatile memory inside a computer system which functions as a server and/or a client in such occasions, namely those for storing a program for a certain period of time. The above-mentioned program may also be the one for achieving part of the above-described function, or may also be the one for achieving the above-described function in collaboration with a program that is already stored in a computer system.

Examples of the program for achieving the information processing function described above include a program that causes a processing apparatus to perform processing that involves determining, from the mass spectrum obtained by mass spectrometry apparatus 1, peaks that are attributable to ribosomal proteins based on a database, generating an approximate curve or an approximate straight line for relative intensities of the peaks, and selecting a peak with a relative intensity from 50 to 150% relative to the approximate curve or the approximate straight line. This program allows for judging whether a protein indicated by a peak on a mass spectrum obtained by mass spectrometry is a ribosomal protein or not, in an easy and simple manner.

The program may cause a processing apparatus to perform processing that involves attributing the selected peak to a ribosomal protein with further consideration of post-translational modification. The program calculates a second calculated m/z value of a peak selected to be of a ribosomal protein, preferably with consideration of post-translational modification. Examples of the post-translational modification that should be considered here include N-terminal methionine cleavage, acetylation, methylation, phosphorylation, glycosylation, oxidation, ubiquitination, SUMOylation, lipidation, and a combination of these, and the like. The second calculated m/z value is compared with the observed m/z values. By this program, the accuracy of ribosomal protein judgement can be enhanced. In addition, information about ribosomal protein amino acid sequence and post-translational modification may also be obtained.

The program may cause a processing apparatus to perform processing that involves, based on the judged ribosomal proteins, identifying the species of the living thing that gives amino acid sequence information of the ribosomal proteins.

EXAMPLES

Next, a more detailed description will be given of the present invention referring to Examples, which are not intended to limit the scope of the present invention.

Experiment 1

*Escherichia coli* (*Escherichia coli* NBRC 3301) was cultured in an LB medium at 30° C. for 8 hours. The cultured bacterial cells were rinsed with ultrapure water by centrifugation, and then disrupted for 3 minutes with the use of zirconia silica beads (diameter, 0.1 mm). The beads and cell fragments were centrifuged (centrifugation conditions, 15000 g for 5 minutes), and the supernatant was recovered, which was for use as a disrupted cell liquid. The resultant disrupted cell liquid was subjected to ultrafiltration (Amicon Ultra 0.5 mL, NMWL 100 KDa, manufactured by Merck), and thereby a concentrated ribosome solution was obtained.

This solution was, as a sample containing ribosomal proteins, subjected to MALDI-MS. Sinapic acid in an amount of 10 mg was dissolved in 1 mL of 50% (v/v) acetonitrile solution containing 1% (v/v) trifluoroacetic acid to prepare a matrix solution. Into a 0.5-mL plastic tube, 7 μL of the matrix solution, 1 μL of an internal standard reagent, and 1 μL of the sample were added and stirred, and 1.0 μL of the resultant was added dropwise onto a stainless steel sample plate, followed by air drying. AXIMA-Performance manufactured by Shimadzu Corporation was used as MALDI-MS, and observation was performed in a positive ion linear mode (flight length, 1.2 m).

Mass spectrum calibration was performed by an internal standard method with the use of peaks of myoglobin $[M+H]^+$ (m/z 16952.6) and [M+2H]2+(m/z 8476.8) and peaks of adrenocorticotropic hormone clip18-39 $[M+H]^+$ (m/z 2465.7). Then, among the peaks of subunit proteins temporarily attributed by the internal standard method, peaks with relatively high intensity and with distinct normal distribution shape were selected, which were then subjected to final calibration by a self calibration method. The m/z value of each peak was obtained by three repeated measurements.

(Attribution Step)

When a peak was observed on a mass spectrum within a margin of error of 200 ppm relative to the first calculated m/z value of $[M+H]^+$ ion of a ribosomal protein obtained from amino acid sequence, it was regarded that the protein was observed. The first calculated m/z values of ribosomal proteins were determined from amino acid sequences retrieved from Swiss-Plot/TrEMBL, with consideration of N-terminal methionine cleavage alone. As a result, 27 peaks were attributed to ribosomal proteins.

(Presumption Step)

Figure 4:
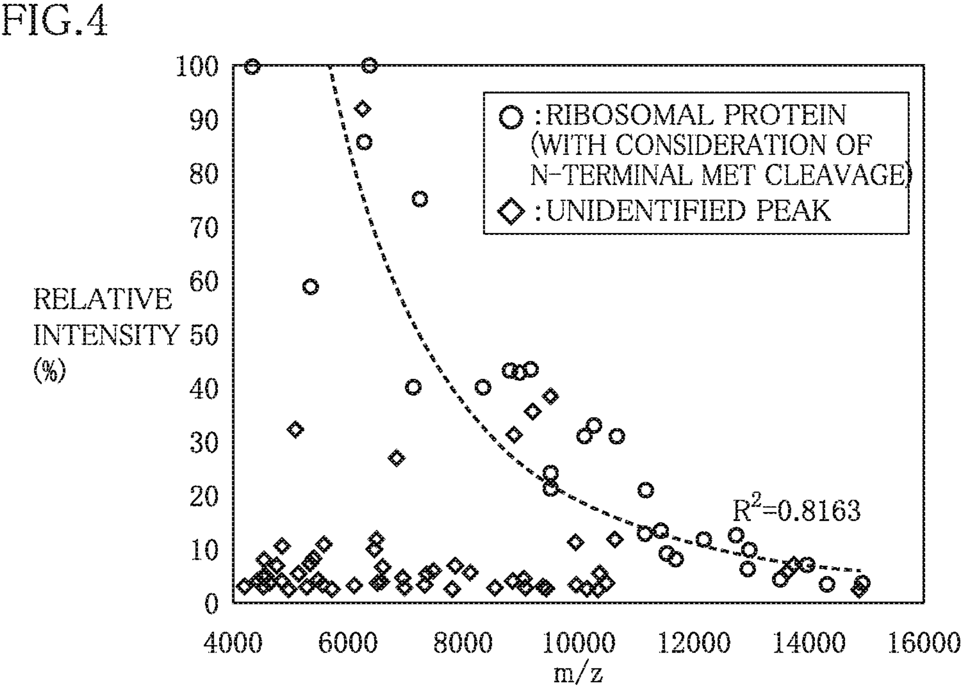
FIG. 4 is a scatter diagram showing observed m/z values and relative intensities of peaks that are attributed to ribosomal proteins and peaks that are not attributed to ribosomal proteins, for Experiment 1.

FIG. 4 is a scatter diagram showing observed m/z values and relative intensities of peaks that were attributed to ribosomal proteins and peaks that were not attributed to ribosomal proteins (unidentified peaks). Although the ribosomal proteins were expected to exist in equimolar amounts, the relative intensities of the peaks attributed to ribosomal proteins were higher on the low mass side and lower on the high mass side due to the mass discrimination effect. An approximate curve was generated for relative intensities of the peaks attributed to ribosomal proteins, which is shown as a broken line in FIG. 4. A peak having a relative intensity close to the approximate curve was presumed to be of a ribosomal protein.

(Verification Step)

Figure 5:
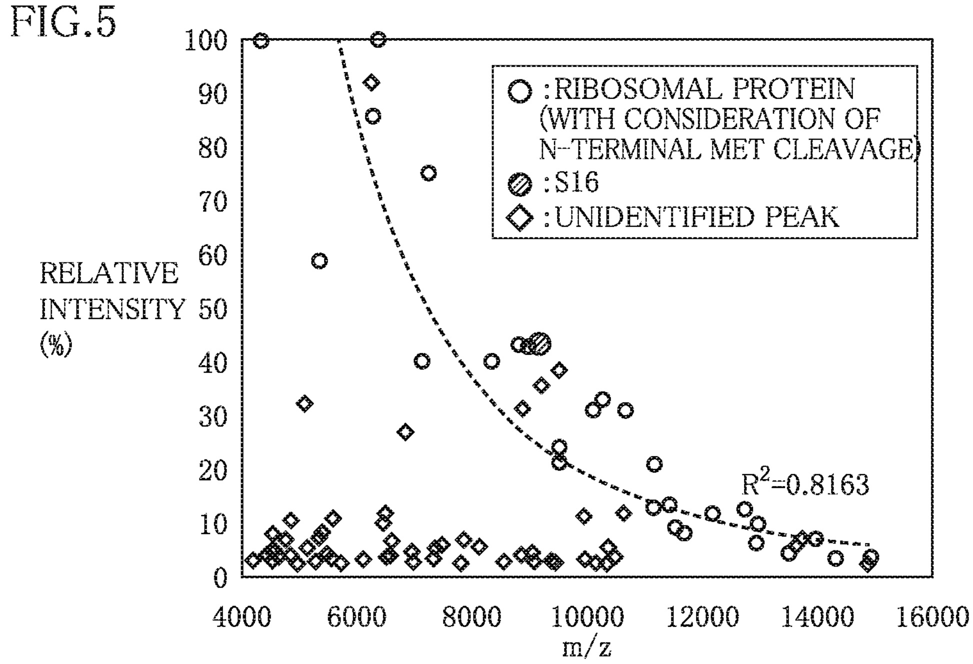
FIG. 5 is a scatter diagram showing observed m/z values and relative intensities of peaks that are newly attributed to ribosomal proteins by a ribosomal protein judgement method, for Experiment 1.

Here, further verification was carried out for a protein presumed to be of a ribosomal protein having an observation peak at m/z 9191. Firstly, as for a ribosomal protein expected to have a peak at m/z 9191, a second calculated m/z value was calculated with consideration of post-translational modification that was not N-terminal methionine cleavage, but the peak at m/z 9191 was not attributed to a ribosomal protein. Here, a document (V. Ryzhov and C. Fenselau, Anal. Chem. 2001, 73, 746-750) reports, in Table 1, that a peak observed at m/z 9191 is of ribosomal protein S16. The second amino acid residue of S16 is valine (V), so, if a law of N terminus is applicable, N-terminal methionine cleavage may have occurred to give a second calculated m/z value of $[M+H]^+$=9060.4. However, no peak was observed corresponding to m/z 9060.4 on the mass spectrum. So, it was considered that S16 may have received an unpredicted post-translational modification to have a peak observed at m/z 9191 instead of at m/z 9060.4. The second calculated m/z value of S16 without N-terminal methionine cleavage is 9191.6. Therefore, an assumption that S16 happened to not receive N-terminal methionine cleavage was adopted, and thus, the peak at m/z 9191 was attributed to S16. FIG. 5 shows relative intensities of peaks that were newly attributed to ribosomal proteins.

Experiment 2

In Experiment 2, ribosomal protein judgement was attempted in the same manner as in Experiment 1 except that a yeast (*Saccharomyces cerevisiae*) was used as bacterial cells. The yeast was cultured in a YM medium (glucose 10 g, peptone 5 g, yeast extract 3 g, malt extract 3 g, distilled water 1 L) at the optimum temperature for 8 hours. Ribosomes were concentrated from the cultured bacterial cells to prepare a sample, which was then subjected to MALDI-MS.

(Attribution Step)

First calculated m/z values determined with consideration of N-terminal methionine cleavage alone based on the amino acid sequence retrieved from Swiss-Plot/TrEMBL were compared with observed m/z values, and, as a result, 27 peaks were attributed to ribosomal proteins.

(Presumption Step)

Figure 6:
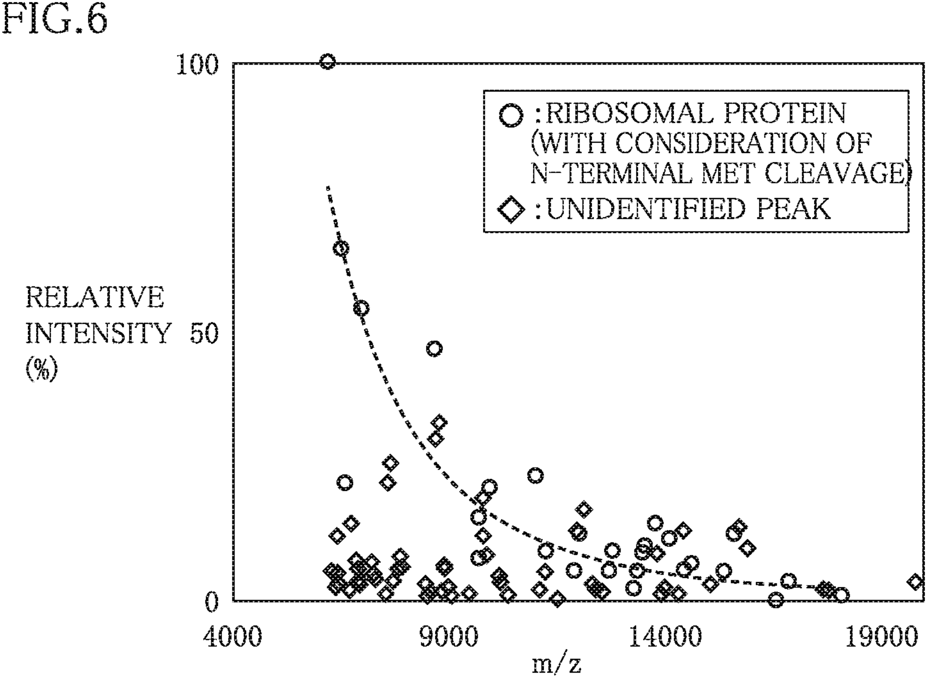
FIG. 6 is a scatter diagram showing observed m/z values and relative intensities of peaks that are attributed to ribosomal proteins and peaks that are not attributed to ribosomal proteins, for Experiment 2.

FIG. 6 is a scatter diagram showing observed m/z values and relative intensities of peaks that were attributed to ribosomal proteins and peaks that were not attributed to ribosomal proteins (unidentified peaks). Although the ribosomal proteins were expected to exist in equimolar amounts, the relative intensities of the peaks attributed to ribosomal proteins were higher on the low mass side and lower on the high mass side due to the mass discrimination effect. An approximate curve was generated for relative intensities of the peaks attributed to ribosomal proteins, which is shown as a broken line in FIG. 6. A peak having a relative intensity close to the approximate curve was presumed to be of a ribosomal protein.

(Verification Step)

Figure 7:
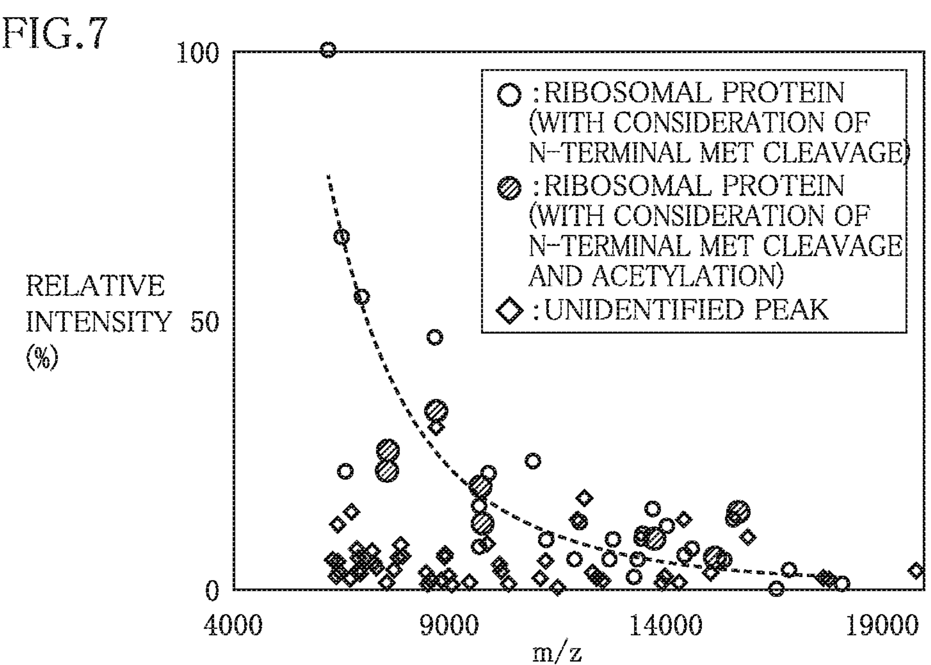
FIG. 7 is a scatter diagram showing observed m/z values and relative intensities of peaks that are newly attributed to ribosomal proteins by a ribosomal protein judgement method, for Experiment 2.

Further verification was carried out for a peak presumed to be of a ribosomal protein having a relative intensity close to the approximate curve. It is known that ribosomal proteins of yeasts receive not only N-terminal methionine cleavage but also acetylation, as post-translational modification. For this reason, a second calculated m/z value of a peak presumed to be of a ribosomal protein was calculated with consideration of N-terminal methionine cleavage and acetylation, and the resultant was compared with the observed m/z values, giving 9 peaks newly attributed to ribosomal proteins. FIG. 7 shows relative intensities of peaks that were newly attributed to ribosomal proteins.

Experiment 3

In Experiment 3, ribosomal protein judgement was attempted in the same manner as in Experiment 1 except that hyphae of a mold (*Aspergillus* Kawachi) were used as bacterial cells. The mold was cultured in a potato dextrose medium at the optimum temperature for 8 hours. Ribosomes were concentrated from the cultured bacterial cells to prepare a sample, which was then subjected to MALDI-MS.

(Attribution Step)

First calculated m/z values determined with consideration of N-terminal methionine cleavage alone based on the amino acid sequence retrieved from Swiss-Plot/TrEMBL were compared with observed m/z values, and, as a result, 16 peaks were attributed to ribosomal proteins.

(Presumption Step)

Figure 8:
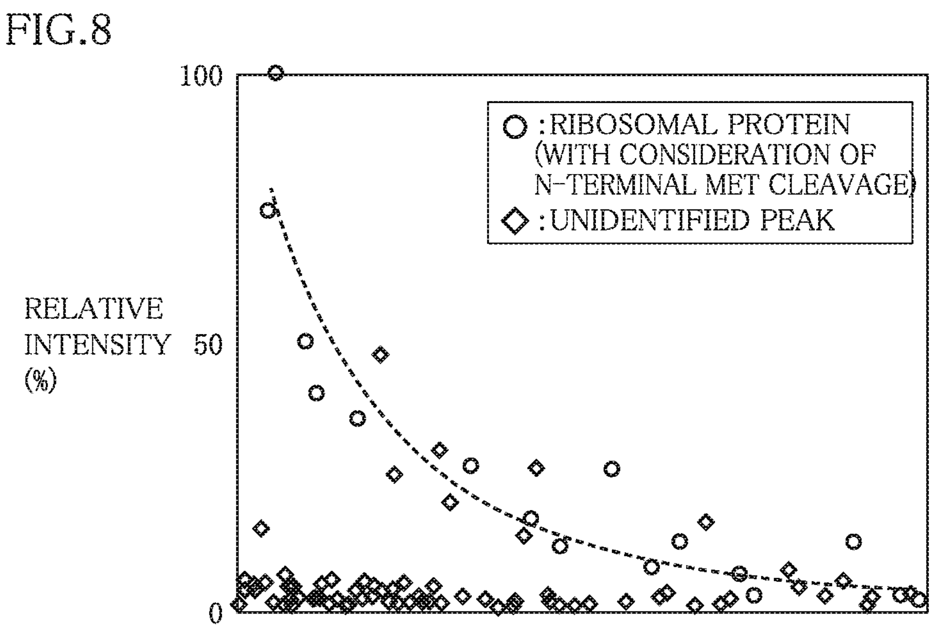
FIG. 8 is a scatter diagram showing observed m/z values and relative intensities of peaks that are attributed to ribosomal proteins and peaks that are not attributed to ribosomal proteins, for Experiment 3.

FIG. 8 is a scatter diagram showing observed m/z values and relative intensities of peaks that were attributed to ribosomal proteins and peaks that were not attributed to ribosomal proteins (unidentified peaks). Although the ribosomal proteins were expected to exist in equimolar amounts, the relative intensities of the peaks attributed to ribosomal proteins were higher on the low mass side and lower on the high mass side due to the mass discrimination effect. An approximate curve was generated for relative intensities of the peaks attributed to ribosomal proteins, which is shown as a broken line in FIG. 8. A peak having a relative intensity close to the approximate curve was presumed to be of a ribosomal protein.

(Verification Step)

Figure 9:
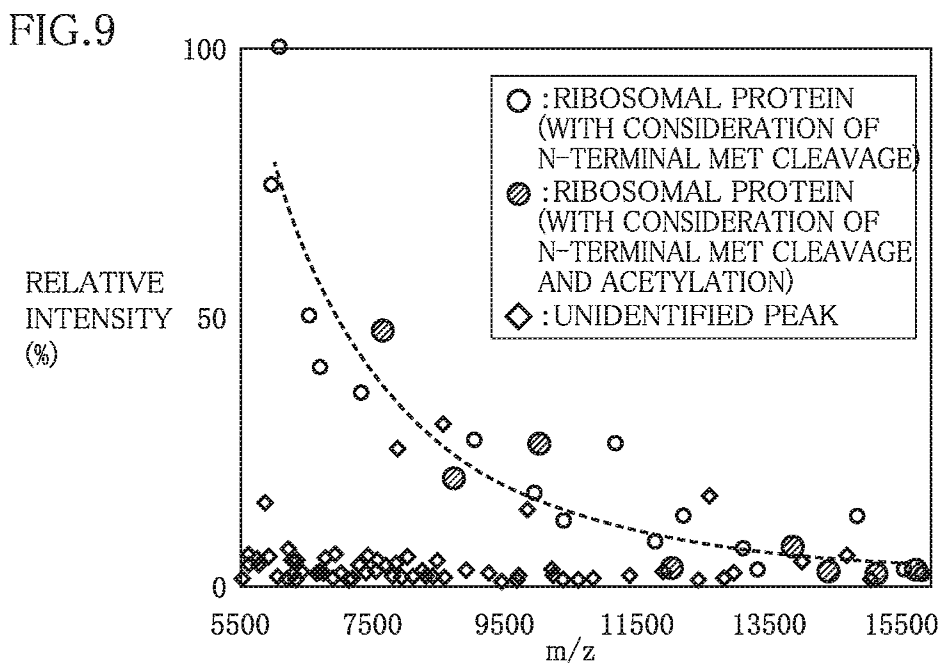
FIG. 9 is a scatter diagram showing observed m/z values and relative intensities of peaks that are newly attributed to ribosomal proteins by a ribosomal protein judgement method, for Experiment 3.

Further verification was carried out for a peak presumed to be of a ribosomal protein having a relative intensity close to the approximate curve. It is known that ribosomal proteins of molds receive not only N-terminal methionine cleavage but also acetylation and methylation, as post-translational modification. For this reason, a second calculated m/z value of a peak presumed to be of a ribosomal protein was calculated with consideration of N-terminal methionine cleavage and acetylation, and the resultant was compared with the observed m/z values, giving 8 peaks newly attributed to ribosomal proteins. FIG. 9 shows relative intensities of peaks that were newly attributed to ribosomal proteins.

[Apsects]

As will be appreciated by those skilled in the art, the above-described example embodiments and Examples are specific examples of the below aspects.

(Item 1)

A ribosomal protein judgement method according to an aspect comprises: an attribution step that involves comparing observed m/z values indicated by peaks on a mass spectrum detected by mass spectrometry of a sample containing ribosomal proteins, with first calculated m/z values based on a database, and attributing at least some of the peaks thus detected to ribosomal proteins; and a presumption step that involves presuming a protein corresponding to a peak with a relative intensity from 50 to 150% relative to an approximate curve or an approximate straight line plotted with relative intensities of the peaks attributed to ribosomal proteins, to be a ribosomal protein.

The ribosomal protein judgement method according to Item 1 allows for easily judging whether a protein indicated by a peak on a mass spectrum obtained by mass spectrometry is a ribosomal protein or not.

(Item 2)

In the ribosomal protein judgement method according to Item 1, the first calculated m/z values are calculated with consideration of post-translational modification.

The ribosomal protein judgement method according to Item 2 allows for more matches to be found between observed m/z values and first calculated m/z values to increase the number of peaks, among other peaks detected on a mass spectrum, that are attributable to ribosomal proteins.

(Item 3)

In the ribosomal protein judgement method according to Item 2, the post-translational modification is N-terminal methionine cleavage.

Because many ribosomal proteins receive N-terminal methionine cleavage as post-translational modification, the ribosomal protein judgement method according to Item 3 allows for more matches to be found between observed m/z values and first calculated m/z values to increase the number of peaks, among other peaks detected on a mass spectrum, that are attributable to ribosomal proteins.

(Item 4)

In the ribosomal protein judgement method according to Item 1 to Item 3, the mass spectrometry is matrix-assisted laser desorption/ionization mass spectrometry.

The ribosomal protein judgement method according to Item 4 allows more ribosomal protein peaks to be detected from a sample, and also allows for decreasing the difference between observed m/z values and first calculated m/z values.

(Item 5)

In the ribosomal protein judgement method according to Item 1 to Item 4, the sample is of eukaryote origin.

The ribosomal protein judgement method according to Item 5 allows even a protein of eukaryote origin, which often has a complex post-translational modification, to be easily judged on whether it is a ribosomal protein or not.

(Item 6)

In the ribosomal protein judgement method according to Item 1 to Item 5, the sample is a ribosomal protein fraction.

The ribosomal protein judgement method according to Item 6 allows for increasing the proportion of ribosomal proteins contained in a sample and thereby enabling more accurate judgement on ribosomal proteins.

(Item 7)

The ribosomal protein judgement method according to Item 1 to Item 6 further comprises a verification step that involves calculating a second calculated m/z value of the protein presumed to be a ribosomal protein, with consideration of post-translational modification, and comparing the second calculated m/z value with the observed m/z values.

The ribosomal protein judgement method according to Item 7 allows for enhancing the accuracy of ribosomal protein judgement. It also allows for obtaining information about ribosomal protein amino acid sequence and post-translational modification.

(Item 8)

A biological species identification method according to an aspect judges ribosomal proteins by the ribosomal protein judgement method according to Item 1 to Item 7, and identifies a species of a living thing that gives amino acid sequence information of the ribosomal proteins.

The ribosomal protein judgement method according to Item 8 allows for performing biological species identification in a way that is easier, more simple, and more accurate.

(Item 9)

In the biological species identification method according to Item 8, the living thing is a microorganism.

The biological species identification method according to Item 9 is suitable for identifying the species of microorganisms.

(Item 10)

A mass spectrometry apparatus according to an aspect comprises: a mass separation member that separates ions based on m/z values; a detection member that detects the ions separated by the mass separation member; a mass spectrum generation member that generates a mass spectrum based on the ions detected by the detection member; and a judgement member that determines, from the mass spectrum, peaks that are attributable to ribosomal proteins based on a database, generates an approximate curve or an approximate straight line for relative intensities of the peaks, and selects a peak with a relative intensity from 50 to 150% relative to the approximate curve or the approximate straight line.

The mass spectrometry apparatus according to Item 10 allows for easily judging whether a protein indicated by a peak on a mass spectrum obtained by mass spectrometry is a ribosomal protein or not.

(Item 11)

The mass spectrometry apparatus according to Item 10 comprises a verification member that attributes the peak thus selected, to a ribosomal protein, with further consideration of post-translational modification.

The mass spectrometry apparatus according to Item 11 allows for enhancing the accuracy of ribosomal protein judgement. It also allows for obtaining information about ribosomal protein amino acid sequence and post-translational modification.

(Item 12)

A program according to an aspect causes a processing apparatus to perform processing that involves determining, from the mass spectrum obtained by the mass spectrometry apparatus, peaks attributable to ribosomal proteins based on a database, generating an approximate curve or an approximate straight line for relative intensities of the peaks, and selecting a peak with a relative intensity from 50 to 150% relative to the approximate curve or the approximate straight line.

The program according to Item 12 allows for judging whether a protein indicated by a peak on a mass spectrum obtained by mass spectrometry is a ribosomal protein or not, in an easier and more simple manner.

(Item 13)

The program according to Item 12 causes a processing apparatus to perform processing that involves attributing the selected peak to a ribosomal protein with further consideration of post-translational modification.

The program according to Item 13 allows for enhancing the accuracy of ribosomal protein judgement. It also allows for obtaining information about ribosomal protein amino acid sequence and post-translational modification.

Although the embodiments of the present invention have been described, the embodiments disclosed herein are illustrative and non-restrictive in any respect. The scope of the present invention is defined by the terms of the claims, and is intended to encompass any modifications within the meaning and the scope equivalent to the terms of the claims.

What is claimed is:

1. A ribosomal protein determination method, comprising:

an attribution step of comparing observed m/z values of peaks in a mass spectrum obtained by mass spectrometry of a sample containing ribosomal proteins with first calculated m/z values of ribosomal proteins based on a database, and attributing, among the obtained peaks, one or more peaks having observed m/z values that match the first calculated m/z values as ribosomal proteins peaks;

a step of generating, from m/z values and relative intensities of the peaks attributed as ribosomal protein peaks, an approximate curve or an approximate straight line representing relative intensity as a function of m/z; and an estimation step of estimating, as a ribosomal protein peak, an unassigned peak that was not attributed as a ribosomal protein peak in the attribution step and that has a relative intensity of 50% to 150% of the relative intensity indicated by the approximate curve or the approximate straight line at the m/z value of the unassigned peak.

2. The ribosomal protein determination method according to claim 1, wherein the first calculated m/z values are calculated with consideration of post-translational modification.

3. The ribosomal protein determination method according to claim 2, wherein the post-translational modification is N-terminal methionine cleavage.

4. The ribosomal protein determination method according to claim 1, wherein the mass spectrometry is matrix-assisted laser desorption/ionization mass spectrometry.

5. The ribosomal protein determination method according to claim 1, wherein the sample is of eukaryote origin.

6. The ribosomal protein determination method according to claim 1, wherein the sample is a ribosomal protein fraction.

7. The ribosomal protein determination method according to claim 1, further comprising:

a verification step of calculating a second calculated m/z value of the protein estimated to be a ribosomal protein, with consideration of post-translational modification, and comparing the second calculated m/z value with the observed m/z values.

8. The ribosomal protein determination method according to claim 1, further comprising:

a step of obtaining information from a database about a candidate protein corresponding to the peak estimated in the estimation step to be a ribosomal protein peak;

a step of applying a modification pattern not considered for the first calculated m/z value, to an amino acid sequence of the candidate protein to recalculate a mass and determine a second calculated m/z value; and a step of, when the second calculated m/z value matches the observed m/z value, attributing the peak as a ribosomal protein peak.

9. The ribosomal protein determination method according to claim 8, wherein when the second calculated m/z value matches the observed m/z value, based on the m/z value of the peak attributed as a ribosomal protein peak, a type of a microorganism is identified.

10. A biological species identification method, wherein ribosomal proteins are determined by the ribosomal protein determination method according to claim 1, and a species of a living thing that gives amino acid sequence information of the ribosomal proteins is identified.

11. The biological species identification method according to claim 10, wherein the living thing is a microorganism.

12. A mass spectrometry apparatus comprising:

a mass separation member that separates ions based on m/z values;

a detection member that detects the ions separated by the mass separation member;

based on the ions detected by the detection member; and a determination member that determines, from the mass spectrum, peaks that are attributable as ribosomal protein peaks based on a database, generates, from relative intensities of the peaks attributed as ribosomal protein peaks, an approximate curve or an approximate straight line representing relative intensity as a function of m/z, and selects an unassigned peak that was not attributed as a ribosomal protein peak by the determination member and that has a relative intensity of 50% to 150% of the relative intensity indicated by the approximate curve or the approximate straight line at the m/z value of the unassigned peak.

13. The mass spectrometry apparatus according to claim 12, comprising a verification member that attributes the peak thus selected, as a ribosomal protein, with further consideration of post-translational modification.

* * * * *